US012612405B2

(12) United States Patent
Park et al.

(10) Patent No.: US 12,612,405 B2
(45) Date of Patent: Apr. 28, 2026

(54) CRYSTALLINE FORM OF 1-(8-BROMOPYRIDO[2,3-E][1,2,4]TRIAZOLO[4,3-A]PYRAZIN-4-YL)-NMETHYLAZETIDIN-3-AMINE HYDROGEN SULFATE MONOHYDRATE

(71) Applicant: JW PHARMACEUTICAL CORPORATION, Seoul (KR)

(72) Inventors: Suha Park, Seoul (KR); Seiho Chin, Seoul (KR)

(73) Assignee: JW PHARMACEUTICAL CORPORATION, Seoul (KR)

( * ) Notice: Subject to any disclaimer, the term of this patent is extended or adjusted under 35 U.S.C. 154(b) by 381 days.

(21) Appl. No.: 18/283,916

(22) PCT Filed: Mar. 29, 2022

(86) PCT No.: PCT/IB2022/052887
§ 371 (c)(1),
(2) Date: Sep. 25, 2023

(87) PCT Pub. No.: WO2022/208345
PCT Pub. Date: Oct. 6, 2022

(65) Prior Publication Data
US 2024/0166648 A1 May 23, 2024

(30) Foreign Application Priority Data
Mar. 30, 2021 (EP) .................................... 21166021

(51) Int. Cl.
| | |
|---|---|
| *C07D 471/14* | (2006.01) |
| *A61K 31/4985* | (2006.01) |
| *A61P 17/00* | (2006.01) |
| *A61P 17/04* | (2006.01) |
| *A61P 29/00* | (2006.01) |
| *A61P 37/08* | (2006.01) |

(52) U.S. Cl.
CPC ........ *C07D 471/14* (2013.01); *A61K 31/4985* (2013.01)

(58) Field of Classification Search
CPC .............. C07D 471/14; A61K 31/4985; C07B 2200/13; A61P 17/00; A61P 17/04; A61P 29/00; A61P 37/08
See application file for complete search history.

(56) References Cited

U.S. PATENT DOCUMENTS

2012/0015953 A1 1/2012 Beauregard et al.

FOREIGN PATENT DOCUMENTS

| | | |
|---|---|---|
| JP | 2000-319277 A | 11/2000 |
| KR | 10-2014-0090984 A | 7/2014 |
| KR | 10-2019-0137013 A | 12/2019 |
| WO | WO-2010-030785 A2 | 3/2010 |

OTHER PUBLICATIONS

Written Opinion from corresponding PCT Application No. PCT/IB2022/052887, Dated Jun. 24, 2022.
International Search Report from corresponding PCT Application No. PCT/IB2022/052887, Dated Jun. 24, 2022.

*Primary Examiner* — Brenda L Coleman
(74) *Attorney, Agent, or Firm* — Harness, Dickey & Pierce, P.L.C.

(57) ABSTRACT

A novel polymorph of 1-(8-bromopyrido[2,3-e][1,2,4]triazolo[4,3-a]pyrazin-4-yl)-N-methylazetidin-3-amine hydrogen sulfate monohydrate is provided along with pharmaceutical compositions comprising the same. Also disclosed is the use of the novel polymorph for the treatment of diseases, such as atopic dermatitis (AD), itch, pruritus and various forms of urticaria for example chronic idiopathic urticaria subtypes.

12 Claims, 9 Drawing Sheets f1 (ppm)

CRYSTALLINE FORM OF 1-(8-BROMOPYRIDO[2,3-E][1,2, 4]TRIAZOLO[4,3-A]PYRAZIN-4-YL)-NMETHYLAZETIDIN-3-AMINE HYDROGEN SULFATE MONOHYDRATE

CROSS-REFERENCE TO RELATED APPLICATIONS

This application is a national phase entry of PCT/IB2022/052887 on Mar. 29, 2022, which claims the benefit of priority from European Patent Application No. 21166021.2 filed on Mar. 30, 2021, the contents of each of which are incorporated herein by reference in its entirety.

SUMMARY OF THE INVENTION

The present invention relates to a novel polymorph of 1-(8-bromopyrido[2,3-e][1,2,4]triazolo[4,3-a]pyrazin-4-yl)-N-methylazetidin-3-amine hydrogen sulfate monohydrate, pharmaceutical compositions comprising the novel polymorph of 1-(8-bromopyrido[2,3-e][1,2,4]triazolo[4,3-a]pyrazin-4-yl)-N-methylazetidin-3-amine hydrogen sulfate monohydrate and to the use of the novel polymorph for the treatment of diseases, such as atopic dermatitis (AD), itch, pruritus and various forms of urticaria for example chronic idiopathic urticaria subtypes, such as cholinergic urticaria. Also provided herein is a method of preparing the crystalline form of the invention.

BACKGROUND OF THE INVENTION

U.S. Pat. No. 9,586,959 relates, among other compounds, to the compound 1-(8-bromopyrido[2,3-e][1,2,4]triazolo[4, 3-a]pyrazin-4-yl)-N-methylazetidin-3-amine and pharmaceutically acceptable salts thereof as well as pharmaceutical compositions comprising the same. That patent also discloses the preparation of a number of salts of the compound of 1-(8-bromopyrido[2,3-e][1,2,4]triazolo[4,3-a]pyrazin-4-yl)-N-methylazetidin-3-amine. 1-(8-bromopyrido[2,3-e][1, 2,4]triazolo[4,3-a]pyrazin-4-yl)-N-methylazetidin-3-amine exhibits a strong histamine 4 receptor inhibitory effect and shows suppressive effects against histamine induced infiltration of inflammatory cells such as mast cells and eosinophils. The compound thus has strong anti-inflammatory and anti-itching effects and is therefore useful for treating a range of diseases such as those disclosed in U.S. Pat. No. 9,586,959, including AD.

A chemical entity may exist in several different crystalline solid forms and these include different polymorphic forms that share the same sum formula (e.g. anhydrates) and different solvates (e.g. monohydrate and dihydrates) of the same chemical entity which do not share the same sum formula. Such crystalline solid forms have distinct crystal structures and vary in physical properties. The different crystalline solid forms can be distinguished from each other by e.g. melting point, XRPD pattern, spectral characteristics (e.g. FT-IR, Raman and SS-NMR), and other physical and chemical properties. Chemical entities can also exist in amorphous form.

The different crystalline solid forms may have distinct physical properties such as e.g. chemical stability, physical stability, hygroscopicity, melting point, solubility, dissolution rate, morphology and bioavailability which make them more or less suitable as the selected active ingredient in a pharmaceutical product.

The actual crystalline form selected therefore plays an important role in the development and manufacture of an active pharmaceutical ingredient. Should a single crystal form be required, it is important that the crystallization process be robust and reliably produce the desired crystalline form in polymorphically pure form and that the crystalline form does not change (e.g. interconvert to a different crystalline form or hydrate/anhydrate) during the relevant manufacturing processes, and/or during storage.

It has been found that one polymorphic form of 1-(8-bromopyrido[2,3-e][1,2,4]triazolo[4,3-a]pyrazin-4-yl)-N-methylazetidin-3-amine hydrogen sulfate monohydrate has superior unexpected advantages compared to other monohydrates, dihydrates and anhydrates of 1-(8-bromopyrido[2, 3-e][1,2,4]triazolo[4,3-a]pyrazin-4-yl)-N-methylazetidin-3-amine hydrogen sulfate, making the crystalline compound of the present invention especially suitable for the preparation of a solid pharmaceutical product. We will hereinafter refer to this polymorphic form of 1-(8-bromopyrido[2,3-e][1,2,4]triazolo[4,3-a]pyrazin-4-yl)-N-methylazetidin-3-amine hydrogen sulfate monohydrate according to the invention as form B.

DETAILED DESCRIPTION OF THE INVENTION

Crystalline forms of the invention and compositions comprising the same In one aspect, the invention relates to crystalline 1-(8-bromopyrido[2,3-e][1,2,4]triazolo[4,3-a]pyrazin-4-yl)-N-methylazetidin-3-amine hydrogen sulfate monohydrate characterized by one or more XRPD reflections at approximately (°2θ) 8.4; 14.7 and 17.0 (±0.2 degrees). In some embodiments the crystalline 1-(8-bromopyrido[2,3-e][1,2,4]triazolo[4,3-a]pyrazin-4-yl)-N-methylazetidin-3-amine hydrogen sulfate monohydrate is characterized by XRPD reflections at approximately (°2θ) 8.4; 14.7 and 17.0 (±0.2 degrees). In some embodiments the XRPD reflections further comprise one or more XRPD reflections at approximately (°2θ) 11.9 and/or 15.1 (±0.2 degrees). In some embodiments the XRPD reflections further comprise one or more XRPD reflections at approximately (°2θ) 23.0 and/or 24.0 (±0.2 degrees). Preferably, the XRPD reflections comprise XRPD reflections at approximately (°2θ) 8.4, 11.9, 14.7, 15.1 and 17.0 (±0.2 degrees). More preferably, the XRPD reflections comprise XRPD reflections at approximately (°2θ) 8.4, 11.9, 14.7, 15.1, 17.0, 23.0 and 24.0 (±0.2 degrees).

In some embodiments, the invention relates to crystalline 1-(8-bromopyrido[2,3-e][1,2,4]triazolo[4,3-a]pyrazin-4-yl)-N-methylazetidin-3-amine hydrogen sulfate monohydrate wherein the crystalline compound has an XRPD pattern essentially similar to the XRPD pattern in FIG. 1.

In some embodiments, the invention relates to crystalline 1-(8-bromopyrido[2,3-e][1,2,4]triazolo[4,3-a]pyrazin-4-yl)-N-methylazetidin-3-amine hydrogen sulfate monohydrate wherein the crystalline compound has an XRPD pattern according to the XRPD pattern in FIG. 1.

In some embodiments the crystalline compound of these embodiments is further characterized by a solid state $^{13}$C CP/MAS NMR spectrum with peaks at one or more of 151.5, 150.6, 145.7, 138.8, 136.1, 126.6, 125.4, 115.7, 59.7, 54.5, 50.7, 36.0 and 32.9 ppm±0.2 ppm. In some embodiments the crystalline compound of these embodiments is characterized by a solid state $^{13}$C CP/MAS NMR spectrum with peaks at 151.5, 150.6, 145.7, 138.8, 136.1, 126.6, 125.4, 115.7, 59.7, 54.5, 50.7, 36.0 and 32.9 ppm±0.2 ppm.

In another aspect the invention relates to crystalline 1-(8-bromopyrido[2,3-e][1,2,4]triazolo[4,3-a]pyrazin-4-yl)-N-methylazetidin-3-amine hydrogen sulfate monohydrate characterized by a solid state $^{13}$C CP/MAS NMR spectrum with peaks at one or more of 151.5, 150.6, 145.7, 138.8, 136.1, 126.6, 125.4, 115.7, 59.7, 54.5, 50.7, 36.0 and 32.9 ppm±0.2 ppm. In some embodiments, the solid state $^{13}$C CP/MAS NMR spectrum comprises peaks at 151.5, 150.6, 145.7, 138.8, 136.1, 126.6, 125.4, 115.7, 59.7, 54.5, 50.7, 36.0 and 32.9 ppm±0.2 ppm.

In some embodiments the invention relates to crystalline 1-(8-bromopyrido[2,3-e][1,2,4]triazolo[4,3-a]pyrazin-4-yl)-N-methylazetidin-3-amine hydrogen sulfate monohydrate wherein the crystalline compound has a $^{13}$C CP/MAS NMR spectrum essentially similar to the $^{13}$C CP/MAS NMR spectrum in FIG. 6.

In some embodiments the invention relates to crystalline 1-(8-bromopyrido[2,3-e][1,2,4]triazolo[4,3-a]pyrazin-4-yl)-N-methylazetidin-3-amine hydrogen sulfate monohydrate wherein the crystalline compound has a $^{13}$C CP/MAS NMR spectrum according to the $^{13}$C CP/MAS NMR spectrum in FIG. 6.

In some embodiments the crystalline compound of these embodiments is further characterized by one or more XRPD reflections at approximately (°2θ) 8.4, 11.9, 14.7, 15.1, 17.0, 23.0 and 24.0 (±0.2 degrees). In some embodiments the crystalline compound of these embodiments is further characterized by XRPD reflections at approximately (°2θ) 8.4, 11.9, 14.7, 15.1, 17.0, 23.0 and 24.0 (±0.2 degrees).

In any of the above aspects and embodiments, the crystalline compound may have a TGA curve comprising an event with an onset at about 90° C. (±10° C.).

In any of the above aspects and embodiments, the crystalline compound may be characterized in that the molar ratio of 1-(8-bromopyrido[2,3-e][1,2,4]triazolo[4,3-a]pyrazin-4-yl)-N-methylazetidin-3-amine to hydrogen sulfuric acid is in the range of from 1:0.8 to 1:1.2, and preferably is approximately 1:1.

In any of the above aspects and embodiments, the crystalline compound may be characterized in that the molar ratio of 1-(8-bromopyrido[2,3-e][1,2,4]triazolo[4,3-a]pyrazin-4-yl)-N-methylazetidin-3-amine hydrogen sulfate to water is in the range from 1:0.8 to 1:1.2, and preferably is approximately 1:1.

Another aspect of the present invention relates to a pharmaceutical composition comprising a crystalline salt compound according to any of the preceding aspects and embodiments of the invention and a pharmaceutically acceptable carrier.

Another aspect of the present invention relates to the crystalline compound or pharmaceutical compositions of the invention described above, for use in the treatment of a disease selected from atopic dermatitis, itch, pruritus and various forms of urticaria. In some embodiments, the forms of urticaria include chronic idiopathic urticaria subtypes. In some embodiments, the chronic idiopathic urticaria subtypes include cholinergic urticaria.

Method of Preparation of Form B

Also provided herein are methods for the preparation of crystalline form B.

In the following embodiments "wt." is a measurement of weight equivalent to the weight of 1-(8-bromopyrido[2,3-e][1,2,4]triazolo[4,3-a]pyrazin-4-yl)-N-methylazetidin-3-amine starting material. In the following embodiments "vol." is a measurement of volume related to the weight of 1-(8-bromopyrido[2,3-e][1,2,4]triazolo[4,3-a]pyrazin-4-yl)-N-methylazetidin-3-amine starting material in kg, wherein 1 vol. is equal to 1 L/kg of 1-(8-bromopyrido[2,3-e][1,2,4]triazolo[4,3-a]pyrazin-4-yl)-N-methylazetidin-3-amine starting material.

4

These Embodiments Include:

1. A method for the preparation of crystalline 1-(8-bromopyrido[2,3-e][1,2,4]triazolo[4,3-a]pyrazin-4-yl)-N-methylazetidin-3-amine hydrogen sulfate monohydrate comprising the step of crystallizing 1-(8-bromopyrido[2,3-e][1,2,4]triazolo[4,3-a]pyrazin-4-yl)-N-methylazetidin-3-amine hydrogen sulfate monohydrate from a solvent system comprising 2-propanol.

2. The method of embodiment 1, wherein the amount of 2-propanol is selected from 20-200 vol., 20-150 vol., 20-100 vol., 20-75 vol., 20-50 vol., 20-35 vol. or 20-30 vol.

3. The method of embodiment 1, wherein the amount of 2-propanol is selected from 25-200 vol., 25-150 vol., 25-100 vol., 25-75 vol., 25-50 vol., 25-35 vol., or 25-30 vol.

4. The method of embodiment 1, wherein the amount of 2-propanol is selected from 30-200 vol., 30-150 vol., 30-100 vol., 30-75 vol., 30-50 vol., or 30-35 vol.

5. The method of embodiment 1, wherein the amount of 2-propanol is approximately 30 vol.

6. The method of any one of embodiments 1-5, wherein said method comprises the step of adding propan-2-ol to a vessel containing 1-(8-bromopyrido[2,3-e][1,2,4]triazolo[4,3-a]pyrazin-4-yl)-N-methylazetidin-3-amine hydrogen sulfate to form a reaction mixture and wherein the reaction mixture has an initial temperature in the range 35-45° C.

7. The method of embodiment 6, wherein said reaction mixture is stirred for 4-5 hours at a temperature in the range 35-45° C.

8. The method of embodiment 6 or 7, wherein said reaction mixture is subsequently cooled to a temperature in the range 0-5° C.

9. The method of embodiment 8, wherein said cooling of the reaction mixture to a temperature in the range 0-5° C. occurs over a period of 1-3 hours, preferably around 1 hour.

10. The method of embodiment 8 or 9, wherein after said reaction mixture has been cooled to a temperature in the range 0-5° C. the reaction mixture is stirred at a temperature in the range of 0-5° C. for 1-2 hours.

11. The method of any one of embodiments 1-10, wherein the 1-(8-bromopyrido[2,3-e][1,2,4]triazolo[4,3-a]pyrazin-4-yl)-N-methylazetidin-3-amine hydrogen sulfate is formed by combining sulfuric acid with a mixture comprising 1-(8-bromopyrido[2,3-e][1,2,4]triazolo[4,3-a]pyrazin-4-yl)-N-methylazetidin-3-amine.

12. The method of embodiment 11, wherein the sulfuric acid is combined with a mixture comprising 1-(8-bromopyrido[2,3-e][1,2,4]triazolo[4,3-a]pyrazin-4-yl)-N-methylazetidin-3-amine and water.

13. The method of embodiment 11 or 12, wherein the amount of sulfuric acid is selected from 0.3-0.6 vol, preferably 0.4 to 0.5 vol, more preferably 0.48 vol.

14. The method of any one of embodiments 11 to 13, wherein said mixture comprises 1-(8-bromopyrido[2,3-e][1,2,4]triazolo[4,3-a]pyrazin-4-yl)-N-methylazetidin-3-amine and water and the amount of water is selected from 6.0-10.0 vol., preferably 7.0-9.0 vol., more preferably 8.0 vol.

15. The method of any one of embodiments 11 to 14, wherein during the process of combining the sulfuric acid with the mixture comprising 1-(8-bromopyrido[2,3-e][1,2,4]triazolo[4,3-a]pyrazin-4-yl)-N-methylazetidin-3-amine, the temperature of the resulting mixture is maintained between 15-30° C.

16. The method of any one of embodiments 11 to 15, wherein after combining the sulfuric acid with the mixture comprising 1-(8-bromopyrido[2,3-e][1,2,4]tri-azolo[4,3-a]pyrazin-4-yl)-N-methylazetidin-3-amine and before the addition of 2-propanol, activated, deco-lourising charcoal is added.

17. The method of embodiment 16, wherein the amount of activated, decolourising charcoal added is selected from 0.1-0.3 wt., preferably 0.2 wt.

18. The method of any one of embodiments 11 to 17, wherein after combining the sulfuric acid with a mixture comprising 1-(8-bromopyrido[2,3-e][1,2,4]tri-azolo[4,3-a]pyrazin-4-yl)-N-methylazetidin-3-amine and optionally adding activated decolourising charcoal, and prior to the addition of 2-propanol, the reaction mixture is heated to 45-55° C.

19. The method of embodiment 18, wherein following the heating of the reaction mixture to 45-55° C., the temperature is maintained at 45-55° C. for around 45 minutes.

20. A method for the preparation of crystalline 1-(8-bromopyrido[2,3-e][1,2,4]triazolo[4,3-a]pyrazin-4-yl)-N-methylazetidin-3-amine hydrogen sulfate monohy-drate, comprising the following steps:

(a) adding sulfuric acid (approximately 0.48 vol.) to a mixture of crude 1-(8-bromopyrido[2,3-e][1,2,4]tri-azolo[4,3-a]pyrazin-4-yl)-N-methylazetidin-3-amine in water (8 vol.) wherein during this addition the temperature is maintained between 15-30° C.;

(b) adding activated decolourising charcoal (0.2 wt.) to the reaction mixture resulting from step (a) followed by heating the reaction mixture to 45-55° C., wherein the temperature of the reaction mixture is maintained between 45-55° C. for around 45 minutes;

(c) filtering the mixture resulting from step (b) and washing the filter cake with water (about 1 vol.) pre-heated to 45-55° C.;

(d) adjusting the temperature of the filtrate obtained from step (c) to between 35-45° C.;

(e) adding 2-propanol (30.0 vol.) to the mixture resulting from step (d) over a period of 60-90 minutes, preferably 60 minutes, whilst maintaining a temperature between 35-45° C. during the addition followed by stirring the reaction mixture at a temperature between 35-45° C. for 4-5 hours;

(f) cooling the reaction mixture obtained from step (e) to a temperature of between 0-5° C. over 1-2 hours, preferably around one hour, and maintaining the reac-tion mixture at a temperature of between 0-5° C. over 1-2 hours; and (g) filtering the mixture resulting from step (f) to obtain crystalline 1-(8-bromopyrido[2,3-e][1,2,4]triazolo[4,3-a]pyrazin-4-yl)-N-methylazetidin-3-amine hydrogen sulfate monohydrate.

21. The method of any one of embodiments 1-20, wherein the crystalline 1-(8-bromopyrido[2,3-e][1,2,4]triazolo [4,3-a]pyrazin-4-yl)-N-methylazetidin-3-amine hydro-gen sulfate monohydrate obtained from said method is characterized by one or more XRPD reflections at approximately (°2θ) 8.4; 14.7 and 17.0 (±0.2 degrees).

22. The method of embodiment 21, wherein the crystal-line 1-(8-bromopyrido[2,3-e][1,2,4]triazolo[4,3-a] pyrazin-4-yl)-N-methylazetidin-3-amine hydrogen sul-fate monohydrate obtained by said method is characterized by XRPD reflections at approximately (°2θ) 8.4; 14.7 and 17.0 (±0.2 degrees).

23. The method of embodiment 21 or 22, wherein the XRPD reflections further comprise one or more XRPD reflections at approximately (°2θ) 11.9 and/or 15.1 (±0.2 degrees), preferably, wherein the XRPD reflec-tions comprise XRPD reflections at approximately (°2θ) 8.4, 11.9, 14.7, 15.1 and 17.0 (±0.2 degrees).

24. The method of any one of embodiments 21-23, wherein the XRPD reflections further comprise one or more XRPD reflections at approximately 23.0 and/or 24.0 (±0.2 degrees), preferably wherein the XRPD reflections comprise XRPD reflections at approxi-mately (°2θ) 8.4, 11.9, 14.7, 15.1, 17.0, 23.0 and 24.0 (±0.2 degrees).

25. The method of any one of embodiments 1-24, wherein the crystalline 1-(8-bromopyrido[2,3-e][1,2,4]triazolo [4,3-a]pyrazin-4-yl)-N-methylazetidin-3-amine hydro-gen sulfate monohydrate obtained from said method is characterized by a solid state $^{13}C$ CP/MAS NMR spectrum with peaks at one or more of 151.5, 150.6, 145.7, 138.8, 136.1, 126.6, 125.4, 115.7, 59.7, 54.5, 50.7, 36.0 and 32.9 ppm±0.2 ppm.

26. The method of any one of embodiments 1-25, wherein the crystalline 1-(8-bromopyrido[2,3-e][1,2,4]triazolo [4,3-a]pyrazin-4-yl)-N-methylazetidin-3-amine hydro-gen sulfate monohydrate obtained from said method is characterized by a solid state $^{13}C$ CP/MAS NMR spectrum with peaks at 151.5, 150.6, 145.7, 138.8, 136.1, 126.6, 125.4, 115.7, 59.7, 54.5, 50.7, 36.0 and 32.9 ppm±0.2 ppm.

Definitions

As used herein the term "rt" or "room temperature" indicates that the applied temperature is not critical and that no exact temperature value have to be kept. Usually, "rt" or "room temperature" is understood to mean temperatures of about 15° C. to about 25° C. [see e.g. EU Pharmacopoeia 7.5, 1.2 (2012)].

The term "solvate" as used herein describes a crystalline compound in which solvent molecules are incorporated into the crystal lattice of the compound in a stoichiometric or non-stoichiometric manner. If the solvent molecules are water the term "hydrate" is used herein.

The type of hydrate depends on the molar ratio of water molecules to 1-(8-bromopyrido[2,3-e][1,2,4]triazolo[4, 3-a]pyrazin-4-yl)-N-methylazetidin-3-amine hydrogen sulfate molecules.

The term "monohydrate" implies 0.8 to 1.2 mol water per mol of 1-(8-bromopyrido[2,3-e][1,2,4]triazolo[4,3-a] pyrazin-4-yl)-N-methylazetidin-3-amine hydrogen sul-fate.

The term "dihydrate" implies 1.8 to 2.2 mol water per mol 1-(8-bromopyrido[2,3-e][1,2,4]triazolo[4,3-a]pyrazin-4-yl)-N-methylazetidin-3-amine hydrogen sulfate.

The term "non-hygroscopic" as used herein indicates that the increase in mass of a drug substance between about 0% to 80% relative humidity is less than 0.2% by weight.

In the context of the present invention, the term "XRPD reflection peak" denotes a particular 2Θ position in an XRPD pattern, wherein the signal-to-noise ratio (calculated according to item 2.2.46 of the European Pharmacopoeia) is greater than 3/1. "Absence of a peak" is herein defined as a peak having an intensity of at most 1%, such as 0.5% or 0.2%, of the highest peak in an XRPD of a sample of the compound of the invention, more preferably no detectable XRPD peak above background signals.

In an XRPD pattern, the main characteristics of diffraction line profiles are 2Θ position, peak height, peak area and shape (characterized by, for example, peak width or asymmetry, analytical function, empirical representation). The 2Θ position is the most important factor as for example the intensity will be affected by sample preparation, and the width of the peaks by particle size. In addition to the diffraction peaks, an X-ray diffraction experiment also generates a more-or-less uniform background in an XRPD pattern, upon which the peaks are superimposed. Besides specimen preparation, other factors contribute to the background, for instance the sample holder, diffuse scattering from air and equipment, other instrumental parameters such as detector noise, general radiation from the X-ray tube, etc. The peak-to-background ratio can be increased by minimizing background and/or by choosing prolonged exposure times.

ABBREVIATIONS

DSC: Differential Scanning Calorimetry
DVS: Dynamic Vapor Sorption
TGA: Thermogravimetric Analysis
XRPD: X-ray Powder Diffraction
$^{13}$C CP/MAS NMR: $^{13}$C cross polarization magic angle spinning nuclear magnetic resonance

Figure 1:
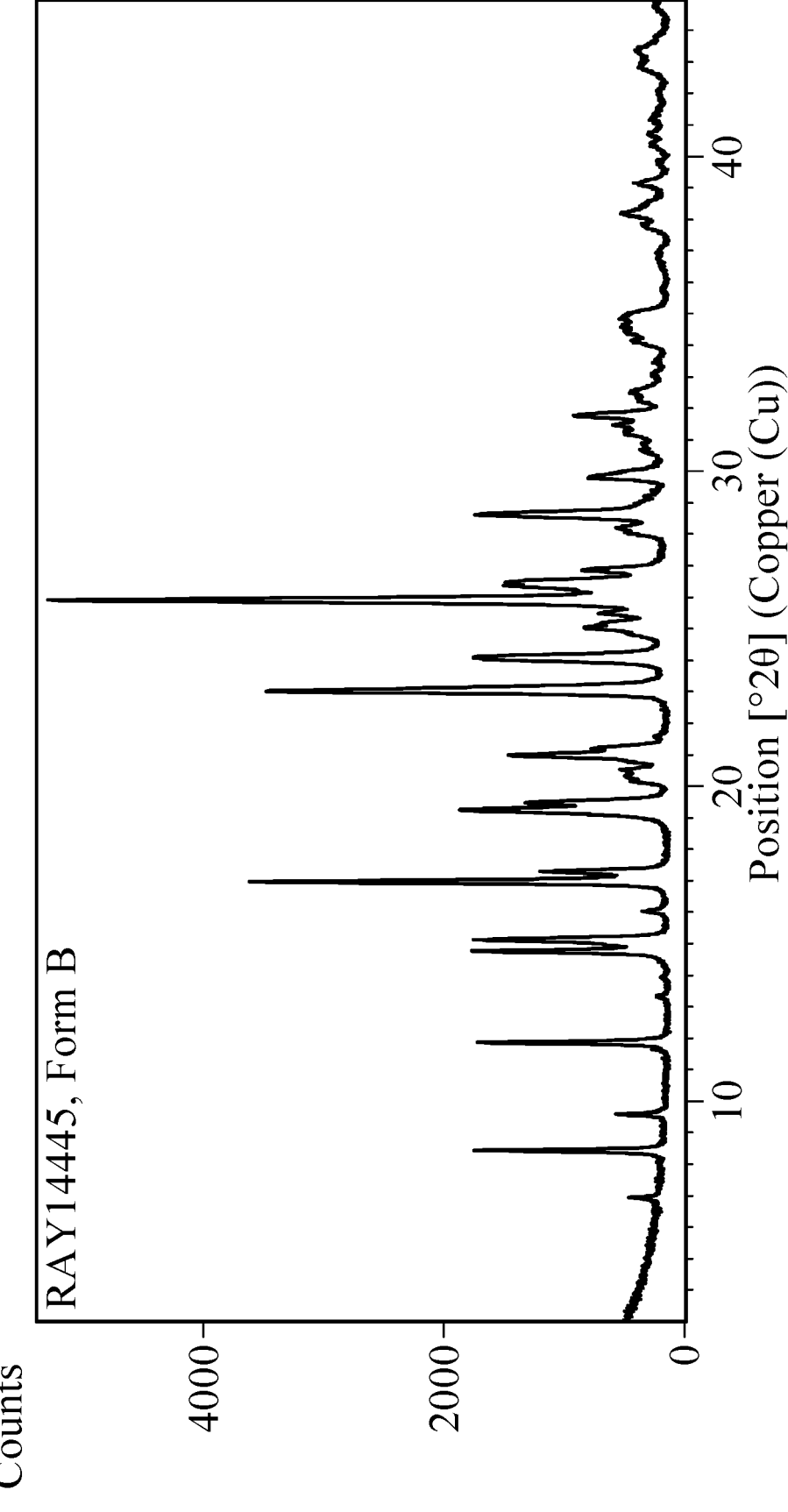
FIG. 1: XRPD pattern of form B
Figure 2:
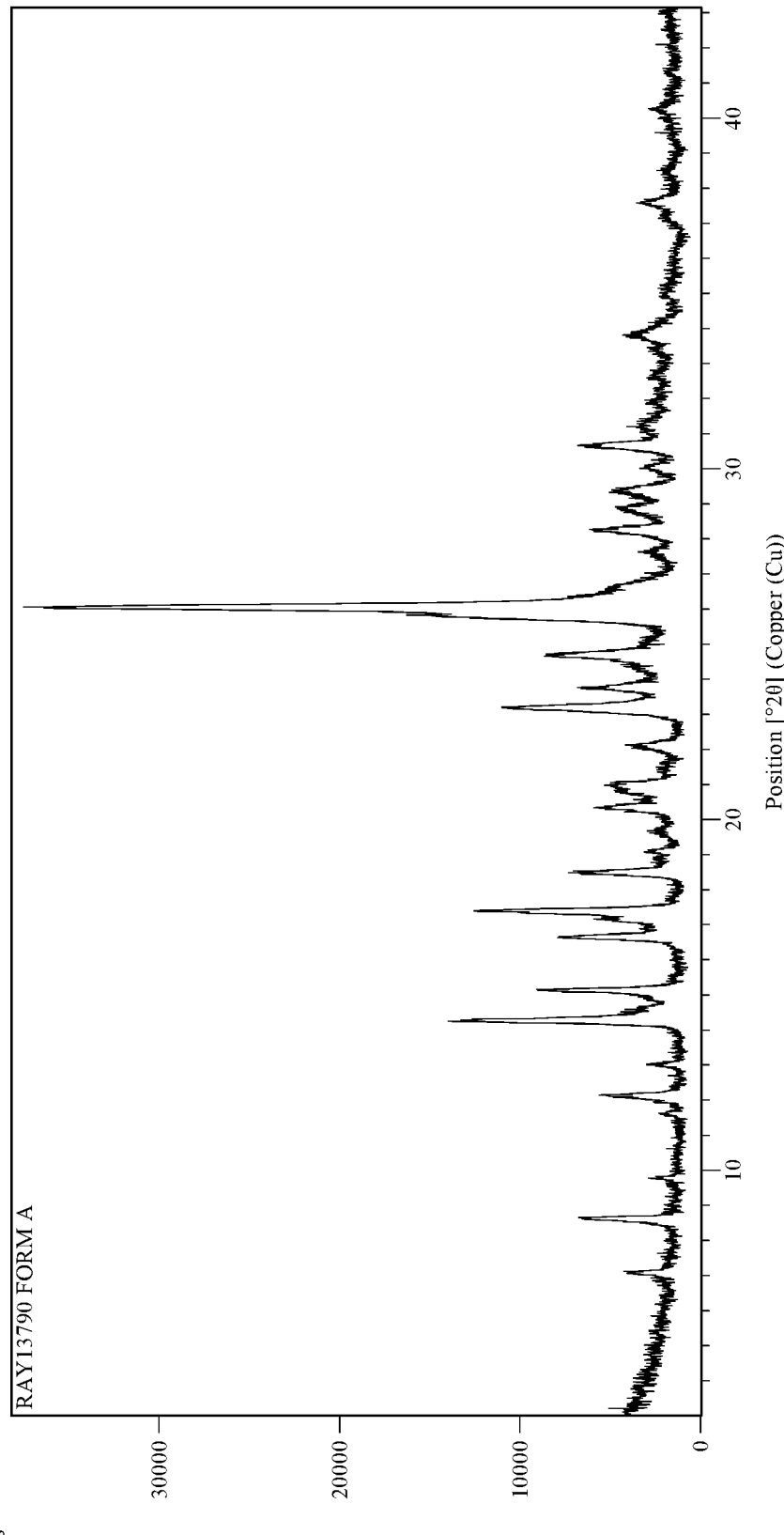
FIG. 2: XRPD pattern of form A
Figure 3:
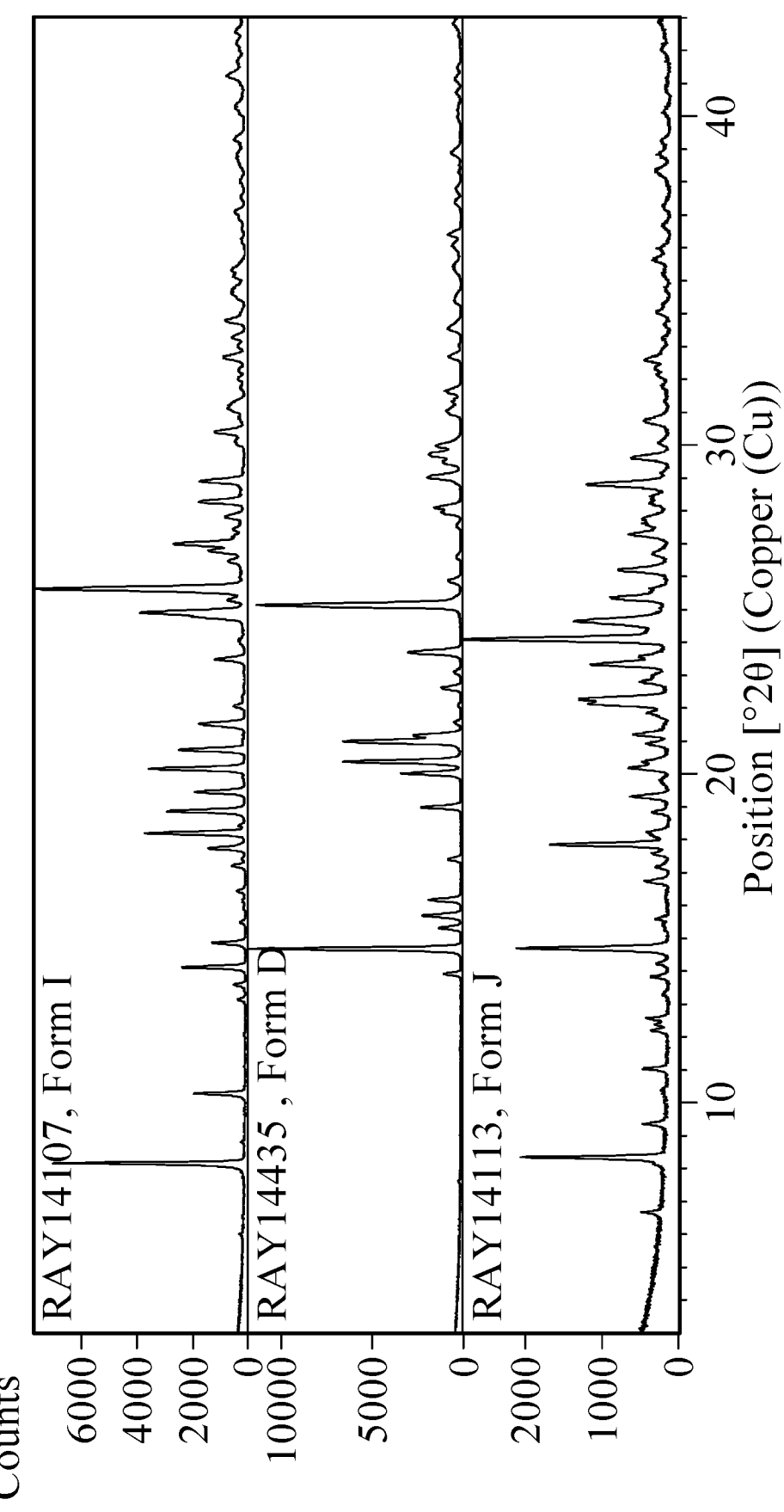
FIG. 3: XRPD patterns of the dihydrates forms D and I together with the DMSO solvate form J
Figure 4:
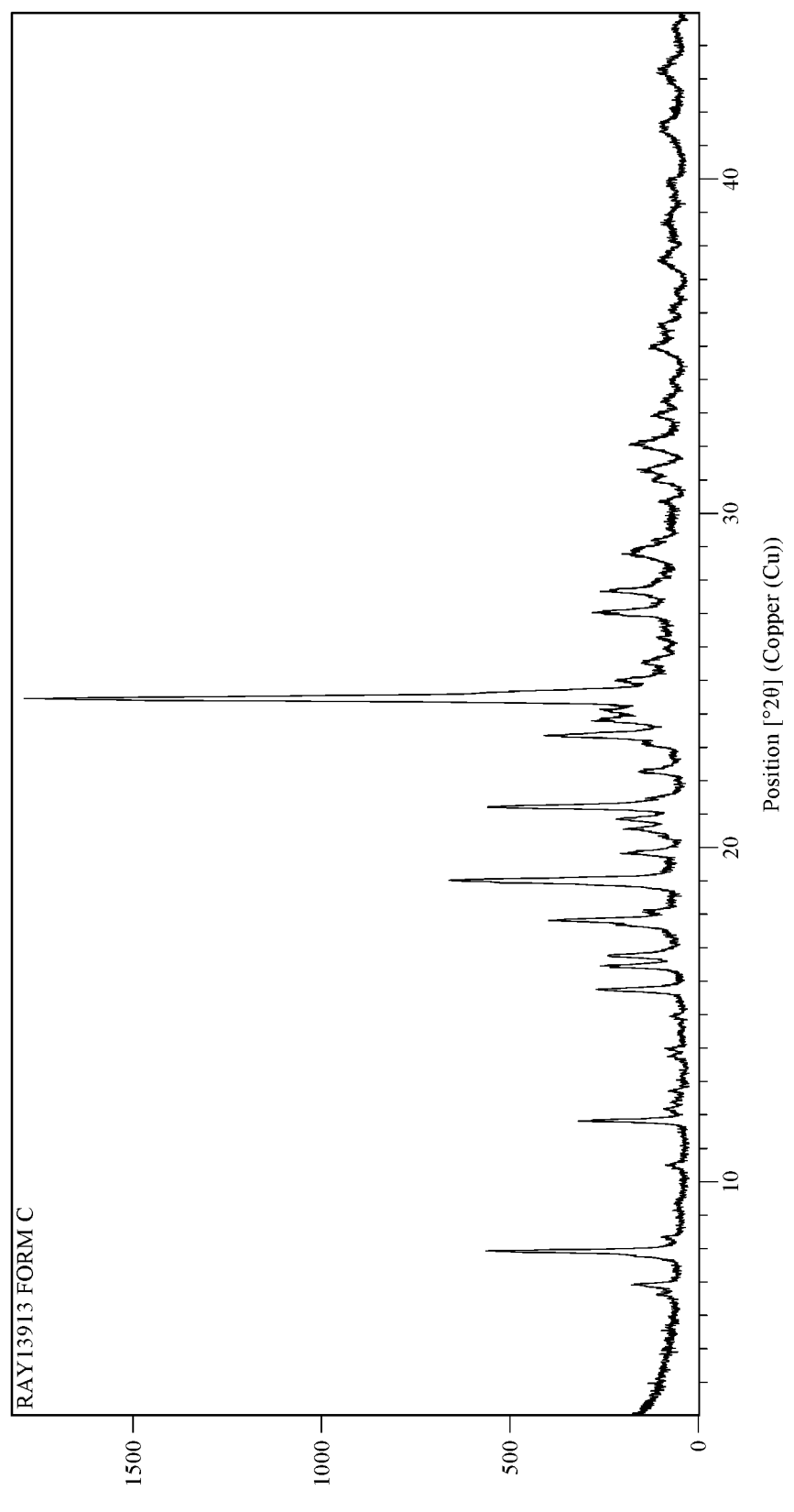
FIG. 4: XRPD pattern of anhydrate form C
Figure 5:
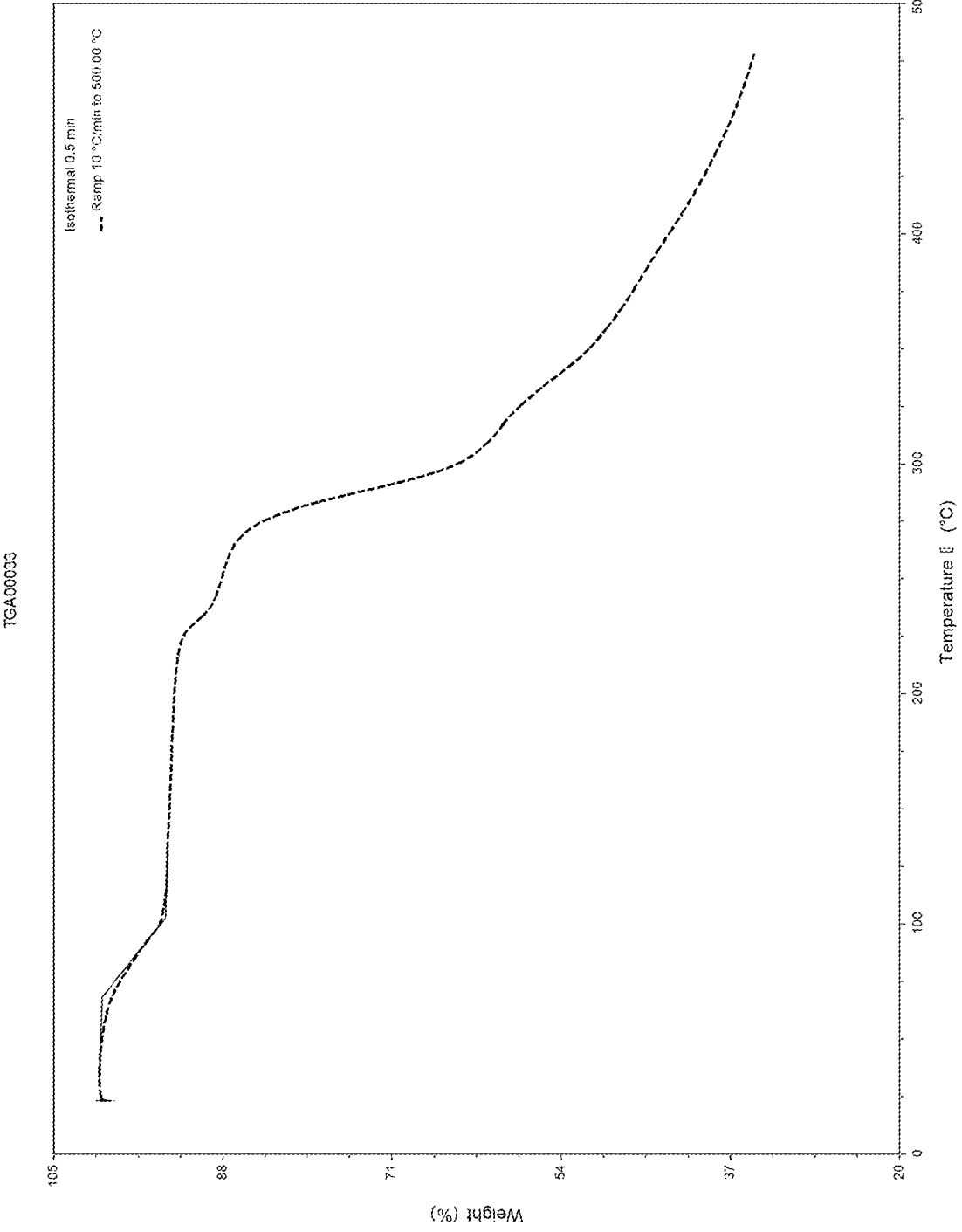
FIG. 5: TGA curve of form F

The technical problem underlying the present invention is to circumvent the drawbacks of other crystalline and/or amorphous forms of 1-(8-bromopyrido[2,3-e][1,2,4]triazolo[4,3-a]pyrazin-4-yl)-N-methylazetidin-3-amine such as, ability to form crystals, filtration properties, solubility, thermodynamic properties, stability issues (e.g. due to water uptake), density, and transformation (e.g. interconversion to other polymorphic forms or hydrates/anhydrates) at varying degrees of humidity and during crystallization processes.

The hydrogen sulfate salt of 1-(8-bromopyrido[2,3-e][1,2,4]triazolo[4,3-a]pyrazin-4-yl)-N-methylazetidin-3-amine has found to exist at least in the form of an anhydrate (form C), two dihydrates (forms D and I) and several polymorphic forms of the monohydrate (forms A, B, F, K, and M).

The table below summarizes interconversions between the different forms and other issues which may be relevant to their use in pharmaceutical compositions:

| Designation | Description | Comments |
| --- | --- | --- |
| Form A | monohydrate | Indication of non-stoichiometric hydrate (around 1 mol water per mol of 1-(8-bromopyrido[2,3-e][1,2,4]triazolo[4,3-a]pyrazin-4-yl)-N-methylazetidin-3-amine hydrogen sulfate) that undergoes solid phase transition to form B at rt over time. |
| Form B | monohydrate | Indication of non-stoichiometric hydrate (around 1 mol water per mol of 1-(8-bromopyrido[2,3-e][1,2,4]triazolo[4,3-a]pyrazin-4-yl)-N-methylazetidin-3-amine hydrogen sulfate). By (DVS) it was demonstrated that form B absorbs 0.2% water at 25° C. between 10 and 80% RH and is therefore considered non-hygroscopic according to Ph. Eur. 5. |
| Form C | anhydrate | DVS has shown that the anhydrate absorbs 0.27% water and is just in the range for being slightly hygroscopic. DVS analysis of form C also showed that when the humidity was increased to 90% a significant increase in hygroscopicity was observed and partial phase transition to the non-stoichiometric hydrate form F was observed. The anhydrate significantly takes up water at increased relative humidity and is therefore not favored for the preparation of a solid medicament. Furthermore, in a liquid environment containing more than 20% water form C will not be stable and therefore can be difficult to precipitate out in the API manufacturing process. |
| Form D | dihydrate | The dihydrate D is not stable in suspension formulations and converts to forms F, I, or N depending on the conditions. Furthermore at r.t. and at ambient conditions form D makes a solid phase transformation to form C. This form is therefore not suitable for use in a pharmaceutical manufacturing process since it would not be stable at r.t. or in e.g. a wet milling process containing solvents such as EtOH. |
| Form F | Non-stoichiometric hydrate | Indication it is a non-stoichiometric hydrate. Under conditions with high water content form F converts to form I. Converts to another form during drying process. The water can very easily be dried off |

-continued

| Designation | Description | Comments |
|---|---|---|
| Form I | dihydrate | Single crystal X-ray analysis shows form I is a nonstoichiometric dihydrate with water situated in channels in the crystal structure. The dihydrate form I is the most stable form in suspensions containing high amounts of water, but it is not stable during drying at room temperature where it converts to form K, which then converts to form C at room temperature. Not suitable in the manufacture of a solid pharmaceutical product as it converts to form C in drying processes. |
| Form K | monohydrate | Form K converts to form C at room temperature. Form K converts to form C in drying processes. It is therefore not suitable in the manufacture of a solid pharmaceutical product |
| Form M | monohydrate | Form M is a monohydrate but loses water and melts at very low temperatures. The TGA curve revealed weight loss already at 50° C. and a broad endothermic event at 44° C. is observed due to water loss and breakdown of the crystal lattice. Due to this low thermal stability form M is not suitable for manufacture of a solid pharmaceutical product. |
| Form J | | Form J is a DMSO solvate not suitable for human use |

The solubility of form B according to Ph. Eur. and USP is as follows: Soluble in dimethyl sulfoxide, sparingly soluble in water, slightly soluble in dimethylformamide, very slightly soluble in methanol, and insoluble in ethanol, 1-propanol, 2-propanol, tert-amyl alcohol, chloroform, xylene, ethyl acetate, acetone, tetrahydrofuran, n-butyl acetate, methyl tert-butyl ether, isopropyl acetate and 1-4-dioxane.

XRPD Patterns

The pure crystalline form B has an XRPD pattern with characteristic peaks (expressed in $2\Theta\pm0.2°$ $2\Theta$(CuKa radiation)) at 8.4, 11.9, 14.7, 15.1, 17.0, 23.0 and 24.0.

The XRPD pattern of form A differs from the XRPD pattern of form B with characteristic XRPD reflection peaks at about $2\Theta$=13.0; 14.3, 16.6, 17.4 and/or 18.5 ($\pm0.2$ degrees).

The XRPD pattern of form C differs from the XRPD pattern of form B with characteristic XRPD reflection peaks at about $2\Theta$=7.9, 15.7, 16.4, 17.8, 21.2, 23.3 and/or 24.4 ($\pm0.2$ degrees).

The XRPD pattern of form D differs from the XRPD pattern of form B with characteristic XRPD reflection peaks at about $2\Theta$=13.9; 15.7, 19.0, 20.0 and/or 25.2 ($\pm0.2$ degrees).

The XRPD pattern of form F differs from the XRPD pattern of form B with characteristic XRPD reflection peaks at about $2\Theta$=12.0; 13.5, 15.5, 17.7; 23.5; 24.3 and/or 27.2 ($\pm0.2$ degrees).

The XRPD pattern of form I differs from the XRPD pattern of form B with characteristic XRPD reflection peaks at about $2\Theta$=8.2; 10.3; 14.1, 18.2, 18.9; 21.5 and/or 23.5 ($\pm0.2$ degrees).

The XRPD pattern of form K differs from the XRPD pattern of form B with characteristic XRPD reflection peaks at about $2\Theta$=9.5; 13.5; 13.8, 18.7 and/or 24.3 ($\pm0.2$ degrees).

The XRPD pattern of form M differs from the XRPD pattern of form B with characteristic XRPD reflection peaks at about $2\Theta$=4.0; 4.6; 6.2 and/or 27.1 ($\pm0.2$ degrees).

$^{13}$C CP/MAS NMR Spectra

Crystalline form B have the following characteristic peaks in a solid state $^{13}$C CP/MAS NMR spectrum: 151.5, 150.6, 145.7, 138.8, 136.1, 126.6, 125.4, 115.7, 59.7, 54.5, 50.7, 36.0, 32.9 ppm±0.2 ppm.

Form I may be distinguished from form B by having the following characteristic peaks in a solid state $^{13}$C CP/MAS NMR spectrum: 151.5, 147.5, 145.9, 140.6, 139.4, 136.9, 127.8, 119.8, 114.9, 60.3, 55.8, 49.6, 35.5, 33.5 ppm±0.2 ppm.

Form F may be distinguished from form B by having the following characteristic peaks in a solid state $^{13}$C CP/MAS NMR spectrum: 152.7, 150.7, 145.4, 139.0, 137.9, 135.9, 125.7, 114.7, 59.5, 55.8, 50.7, 36.2, 33.2 ppm±0.2 ppm.

Some formulations, e.g. tablets may contain ingredients that have XRPD reflection peaks in the same position or area as the crystalline salt of the invention or have broad peaks. These may hide some of the XRPD pattern or peaks of the crystalline salt of the invention when the XRPD experiment is performed on a formulation comprising the crystalline salt of the invention as opposed to the pure crystalline salt alone. This means that one cannot always see all XRPD reflection peaks of the crystalline salt of the invention when an XRPD experiment is performed on a formulation of the salt.

Thus, according to one embodiment, the invention relates to a pharmaceutical composition comprising a crystalline salt as defined herein together with pharmaceutically acceptable vehicle, excipient or pharmaceutically acceptable carrier(s), wherein said pharmaceutically acceptable vehicle, excipient or pharmaceutically acceptable carrier(s) comprises one or more ingredients which exhibit XRPD reflection peaks including one or more XRPD reflection peaks that overlap with and hide one or more XRPD reflection peaks of the crystalline salt. The same issues may arise with solid state NMR where for example intense signals from a cellulose component should be expected in the spectral region 60-110 ppm and the peaks from stearate will be seen in the spectral region 15-40 ppm—along with a carbonyl peak around 172 ppm.

The absence of other crystalline forms of 1-(8-bromopyrido[2,3-e][1,2,4]triazolo[4,3-a]pyrazin-4-yl)-N-methylazetidin-3-amine hydrogen sulfate can be tested by comparing an XRPD pattern taken of any crystalline 1-(8-bromopyrido[2,3-e][1,2,4]triazolo[4,3-a]pyrazin-4-yl)-N-methylazetidin-3-amine hydrogen sulfate with an XRPD pattern of form B as obtained e.g. from example 1 and shown in FIG. 1. For such a comparison, the XRPD pattern shown in FIG. 1 can be taken as an XRPD pattern of 100% pure crystalline compound of form B of the present invention. 1-(8-bromopyrido[2,3-e][1,2,4]triazolo[4,3-a]pyrazin- 4-yl)-N-methylazetidin-3-amine and its hydrogen sulfate salt have very low solubilities in common solvents used for crystallizations including alcohols such that large amounts of alcohol have previously had to be used for the crystallization process. In addition other process parameters such as temperature, time, water/organic solvent ratio have to be controlled in order to obtain desired polymorphic form B of 1-(8-bromopyrido[2,3-e][1,2,4]triazolo[4,3-a]pyrazin-4-yl)-N-methylazetidin-3-amine hydrogen sulfate monohydrate.

It has now been found that a large-scale robust process by which the monohydrate form B can be obtained using a scalable amount of solvent has recently been developed and is an embodiment of the present invention A further aspect of the present invention is directed to a pharmaceutical composition comprising the crystalline compound of the present invention (Form B) and at least one pharmaceutically acceptable excipient. The pharmaceutical composition may be an oral dosage form, preferably a tablet and/or capsule.

In addition, the present invention relates to the use of the crystalline compound of the present invention (Form B) for the preparation of a solid medicament.

In another embodiment the present invention relates to solid pharmaceutical compositions comprising an effective amount of the crystalline compound of the present invention (Form B) and a pharmaceutically acceptable carrier as well as to processes of preparing the same.

Moreover, the present invention is directed to the pharmaceutical composition of the present invention and/or the crystalline compound of the present invention (Form B) for use in the treatment of any of the disease or disorders mentioned in U.S. Pat. No. 9,586,959, including diseases and disorders such as atopic dermatitis (AD), itch, pruritus and any of the various types of urticaria.

The pharmaceutical compositions of the present invention comprising the crystalline compound of the present invention (Form B) may further comprise one or more pharmaceutically acceptable excipients. Such excipients are preferably selected from the group consisting of diluents, sweeteners, buffering agents, glidants, flowing agents, flavouring agents, lubricants, preservatives, surfactants, wetting agents, binders, disintegrants and thickeners. Other excipients known in the field of pharmaceutical compositions may also be used. Furthermore, the pharmaceutical composition may comprise a combination of two or more excipients also within one of the members of the above-mentioned group.

Suitable binders which can be used for the pharmaceutical compositions of the present invention comprising the crystalline compound of the present invention (Form B), further comprise e.g. alkylcelluloses such as methylcellulose, hydroxyalkylcelluloses such as hydroxymethylcellulose, hydroxyethylcellulose, hydroxypropylcellulose and hydroxybutylcellulose, hydroxyalkylalkylcelluloses such as hydroxyethylmethylcellulose and hydroxypropylmethylcel-lulose, carboxyalkylcelluoses such as carboxymethylcellulose, alkali metal salts of carboxyalkylcelluloses such as sodium carboxymethylcellulose, carboxyalkylalkylcellulo-ses such as carboxymethylethylcellulose, carboxyalkylcel-lulose esters, starches such as starch 1551, pectins such as sodium carboxymethylamylopectin, chitin derivatives such as chitosan, heparin and heparinoids, polysaccharides such as alginic acid, alkali metal and ammonium salts thereof, carrageenans, galactomannans, tragacanth, agar-agar, gum arabic, guar gum and xanthan gum, polyacrylic acids and the salts thereof, polymethacrylic acids and the salts thereof, methacrylate copolymers, polyvinylalcohol, polyvinylpyrrolidone, copolymers of polyvinylpyrrolidone with vinyl acetate, polyalkylene oxides such as polyethylene oxide and polypropylene oxide and copolymers of ethylene oxide and propylene oxide, e.g. poloxamers and poloxamines, copovi-done.

Suitable diluents which can be used for the pharmaceutical compositions of the present invention comprising the crystalline compound of the present invention (Form B) further comprise e.g. calcium carbonate, dibasic calcium phosphate, dibasic calcium phosphate dihydrate, tribasic calcium phosphate, calcium sulphate, microcrystalline cellulose including silicified microcrystalline cellulose, powdered cellulose, dextrates, dextrin, dextrose excipient, fructose, kaolin, lactitol, lactose anhydrous, lactose monohydrate, mannitol, sorbitol, starch, modified starch, sodium chloride, sucrose, compressible sugar, confectioner's sugar, a spray-dried mixture of lactose monohydrate and microcrystalline cellulose (75:25), commercially available as Microcelac®, a co-processed spray-dried mixture of microcrystalline cellulose and colloidal silicon dioxide (98:2), commercially available as Prosolv®.

Suitable glidants which can be used for the pharmaceutical compositions of the present invention comprising the crystalline compound of the present invention (Form B) further comprise e.g. talc, colloidal silicon dioxide, starch and magnesium stearate.

Suitable disintegrants which can be used for the pharmaceutical compositions of the present invention comprising the crystalline compound of the present invention (Form B) further comprise e.g. starch, ion exchange resins, e.g. Amberlite, cross-linked polyvinylpyrrolidone, modified cellulose gum, e.g croscarmellose sodium, sodium starch glycolate, sodium carboxymethylcellulose, sodium dodecyl sulphate, modified corn starch, microcrystalline cellulose, magnesium aluminium silicate, alginic acid, alginate and powdered cellulose.

Suitable lubricants which can also be used for the pharmaceutical compositions of the present invention comprising the crystalline compound of the present invention (Form B) further comprise e.g. magnesium stearate, calcium stearate, stearic acid, talc, polyethylene glycol, sodium lauryl sulphate and magnesium lauryl sulphate.

In the following the present invention will be described in further detail by illustrative, non-limiting examples.
Description of the Test Methods Used to Characterize the Polymorphic Forms Disclosed Herein
XRPD:

XRPD patterns were collected with a PANalytical X'pert PRO MPD diffractometer using an incident Cu Kα radiation and operating at 45 kV and 40 mA. The XRPD patterns were collected in the 2θ range from 3 to 45 degrees with a step size of 0.007°, counting time of 148.93 s and in transmission geometry. In the incident beam path, an elliptically graded multilayer mirror together with a 4 mm fixed mask, fixed anti-scatter slit 1° and fixed divergence slits of ½° were placed to line focus the Cu Kα X-rays through the sample and onto the detector. At the diffracted beam path, a long antiscatter extension were placed to minimize the background generated by air. Furthermore, Soller slits of 0.02 rad were placed on both the incident and diffracted beam paths to minimize broadening from axial divergence.

The intensities measured in XRPD may vary considerably between samples of the same crystal structure due to orientation in the sample (orientation effects). The intensities measured in XRPD will also include experimental error. Measured peak intensities will vary depending on various experimental factors such as the equipment used, the testing conditions employed, the size of the sample, the crystallinity of the material (the degree of structural order) and the sample preparation.

The sample was placed on a 3 μm thick foil on a 96-high throughput well plate stage and oscillated in the X direction for better particle statistics. The diffraction patterns were collected using a PIXel RTMS detector with active length of 3.347° and located 240 mm from the sample.

SS-NMR

Solid-state $^{13}$C cross polarization (CP) magic angle spinning (MAS) NMR spectra were recorded using a Bruker Avance 400 NMR instrument operating at Larmor frequencies of 100.6 and 400.13 MHz for $^{13}$C and $^{1}$H, respectively. The experiments were conducted using a double tuned CP/MAS probe equipped for 4 mm (outer diameter, o.d.) spinners. All samples were packed in 4 mm (o.d.) zirconia spinners. The CP/MAS NMR spectra were recorded using with variable amplitude cross polarization and high-power proton decoupling (TPPM) during acquisition. The operation conditions were: temperature: 294 K; contact time: 7 ms; recycle delay: 64 s, 128-840 scans; spin rate of 9 kHz. Chemical shifts were referenced to an external sample of α-glycine (carbonyl carbon chemical shift assigned to 176.5 ppm relative to the signal of tetramethylsilane).

TGA

TGA experiments were conducted using a TGA550 instrument from TA Instruments. About 1-10 mg of sample was loaded into a ceramic pan for the measurements. The sample temperature was ramped from 25 to 500° C. at 10° C./min. Nitrogen was used as the purge gas at a flow rate of 50 mL/min.

DSC

DSC analyses were carried out on a TA Instruments Q20 Differential Scanning Calorimeter. Accurately weighed samples were placed in crimped aluminum pans. Each sample was heated under nitrogen at a rate of 10° C./minute to a maximum of 300° C. Indium metal was used as the calibration standard.

DVS:

Instrument: DVS Advantage

Methods: About 5 mg of the substance was added into Al pan and exposed to stepwise RH changes during two consecutive cycles according to; 20-30-40-50-60-70-80-70-60-50-40-30-20-10-0-10-20-30-40-50-60-70-80-90-80-70-60-50-40-30-20-10-0/RH using open loop mode. The experiments were performed using a gas flow rate of 200 ml/min and at 25° C. The dm/dt criteria applied was 0.001 weight-%/min during a 5 minutes window, with a maximum allowed time of 150 minutes for all steps, except for the steps at 0% RH which had no criteria but were set to 6 h.

EXAMPLES

Example 1: Preparation of 1-(8-bromopyrido[2,3-e] [1,2,4]triazolo[4,3-a]pyrazin-4-yl)-N-methylazetidin-3-amine hydrogen sulfate monohydrate form B A reactor was charged with crude 1-(8-bromopyrido[2,3-e][1,2,4]triazolo[4,3-a]pyrazin-4-yl)-N-methylazetidin-3-amine (17.04 kg, 1.0 equiv). Purified water (136.3 L, 8.0 wt. 8.0 vol) was added under a nitrogen atmosphere using a pipe and an in-line filter. The reaction mixture was agitated without excessive splashing. The temperature was adjusted to 20.0° C. (target 15-20° C.). Concentrated sulfuric acid (15.1 kg, 0.88 wt, 0.48 vol) was charged carefully via a pipe with an in-line filter while maintaining the temperature between 15-30° C. The end temperature for this addition was 19.6° C. The line was rinsed with purified water (17.2 L, 1.0 wt, 1.0 vol).

Activated decolourising charcoal (3.4 kg, 0.2 wt) was then charged to the reactor. The temperature was adjusted to 49.0° C. (target 45-55° C.). The reaction mixture was stirred for 15-45 minutes (target 30 minutes) before it was filtered and collected in a receiver vessel. Purified water (17.2 L, 1.0 wt, 1.0 vol) was heated to 45-55° C. (target 50° C.) and then used to wash the filter cake. The clarified filtrate was transferred back to the original vessel and the temperature of the filtrate adjusted to 40.6° C. (target 35-45° C.).

2-Propanol (403.8 kg, 23.7 wt, 30.0 vol) was charged to the reactor over 71 minutes (target 60-90 minutes) while maintaining the temperature at 35-45° C. (target 40° C.). The end temperature for the addition of 2-propanol was 39.2° C. The reaction mixture was stirred for 4 hours and 24 minutes (target 4-5 hours) at 35-45° C., the end temperature was 40.6° C. Then, the temperature was adjusted to 3.5° C. over 2 hours and 3 minutes (target end temperature of 0-5° C. over a target time of 1-2 hours). The reaction mixture was stirred for 1 hour and 53 minutes at 3.5° C. (target stirring time of 1-2 hours at a target temperature of 0-5° C.). The reaction mixture was filtered over a 1-2 μm cloth at 0-5° C.

2-propanol (27.3 kg, 1.6 wt, 2.0 vol) was cooled to 0-5° C. then added to the reaction vessel for washing. The content of the vessel was cooled to 2.8° C. (target temperature of 0-5° C.) before it was used to wash the filter cake. The filter cake was dried on the filter using a nitrogen flow until no further filtrate was passing (2 hours and 25 minutes). The content of the filter was dried under vacuum for at least 12 hours at up to 25° C. until the 2-propanol was 0.35% w/w. After 12 hours and 12 minutes a sample contained 0.09% w/w.

This method afforded 12.0 kg of 1-(8-bromopyrido[2,3-e][1,2,4]triazolo[4,3-a]pyrazin-4-yl)-N-methylazetidin-3-amine hydrogen sulfate monohydrate as form B.

Figure 6:
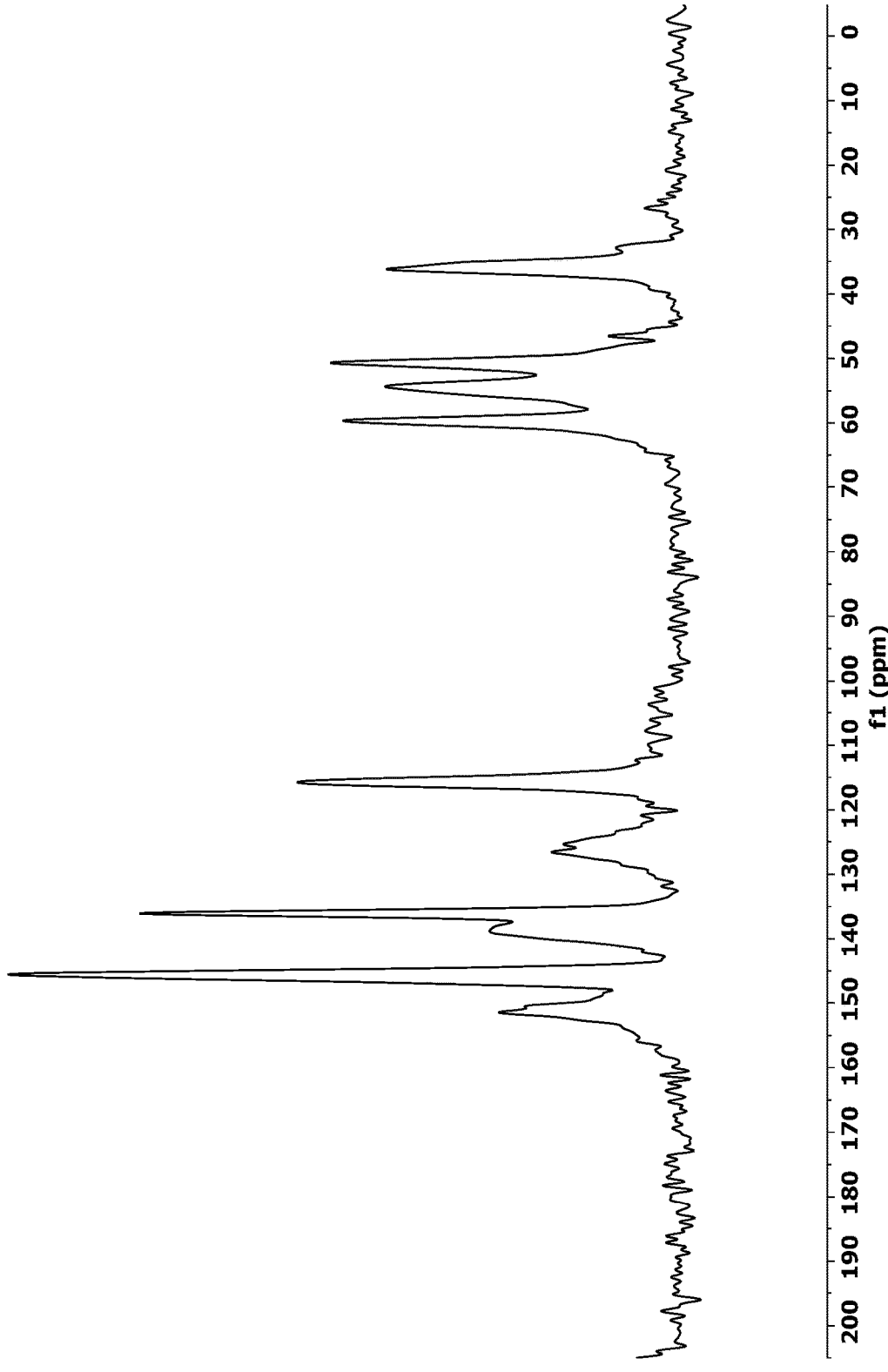
FIG. 6: $^{13}$C CP/MAS NMR spectrum of form B.
Figure 7:
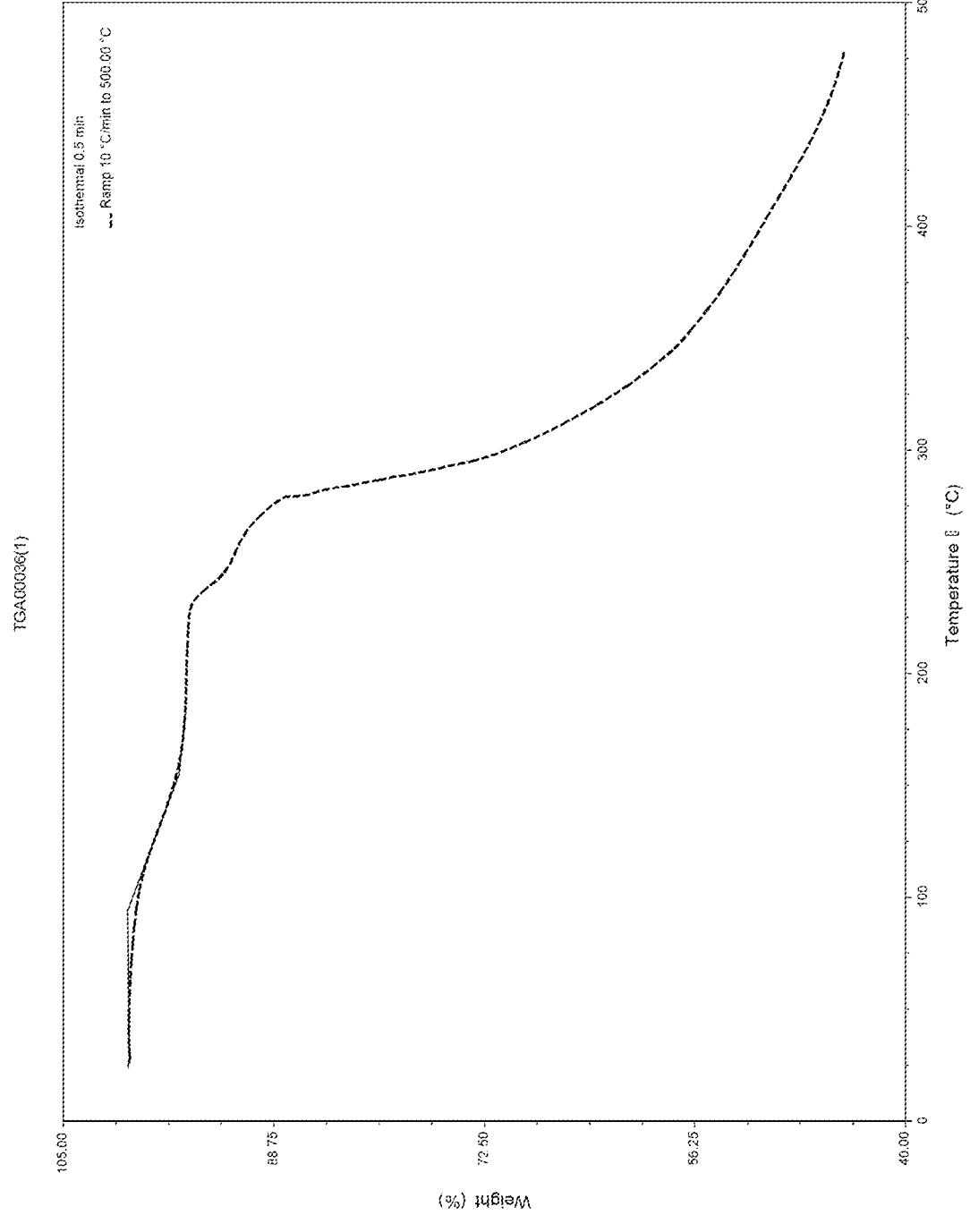
FIG. 7: TGA curve of form B. The crystalline form B is a monohydrate and has a weight loss before decomposition corresponding to approximately 1 mol of water per mol of 1-(8-bromopyrido[2,3-e][1,2,4]triazolo[4,3-a]pyrazin-4-yl)-N-methylazetidin-3-amine hydrogen sulfate as shown in FIG. 7.
Figure 8:
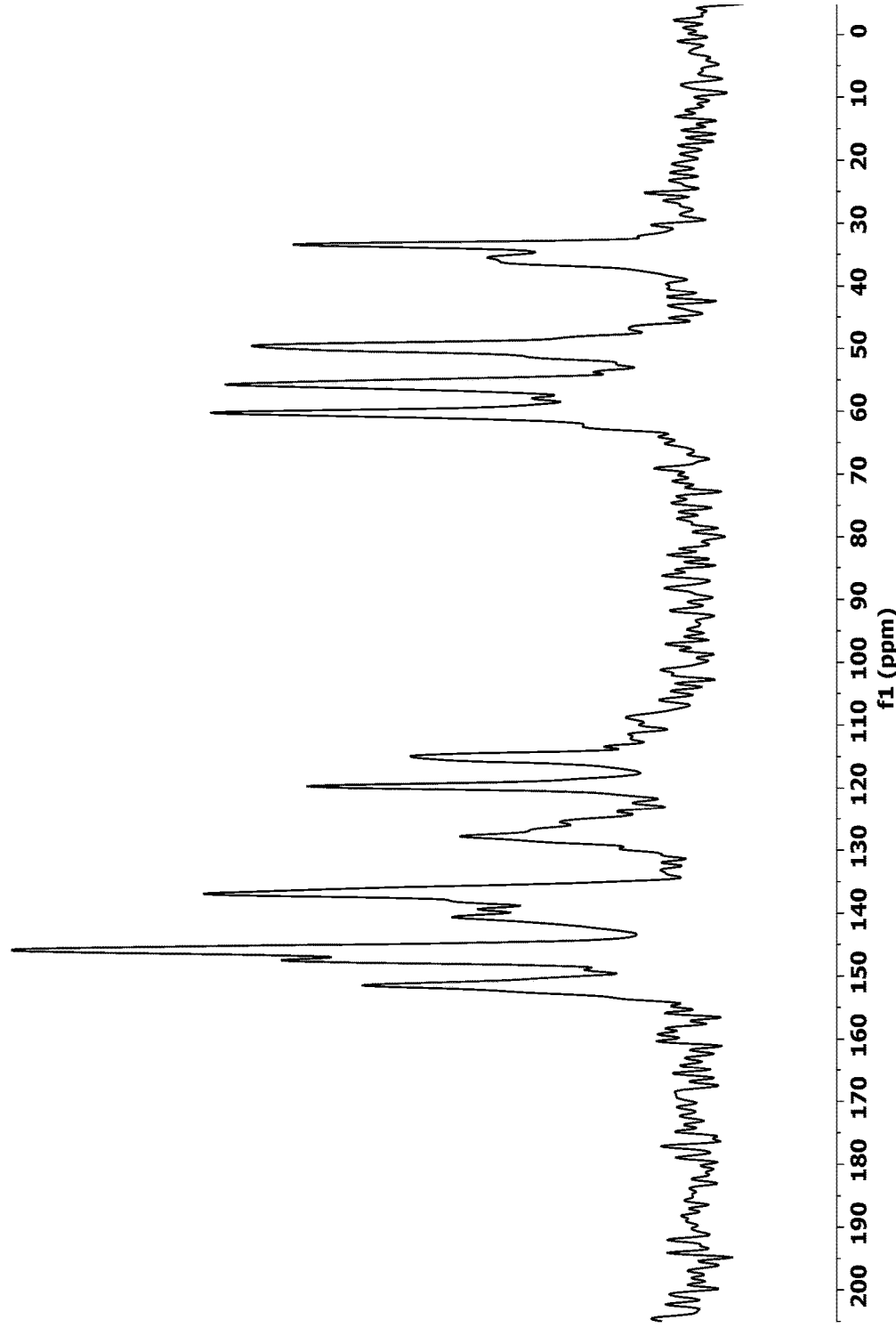
FIG. 8: $^{13}$C CP/MAS NMR spectrum of form I.
Figure 9:
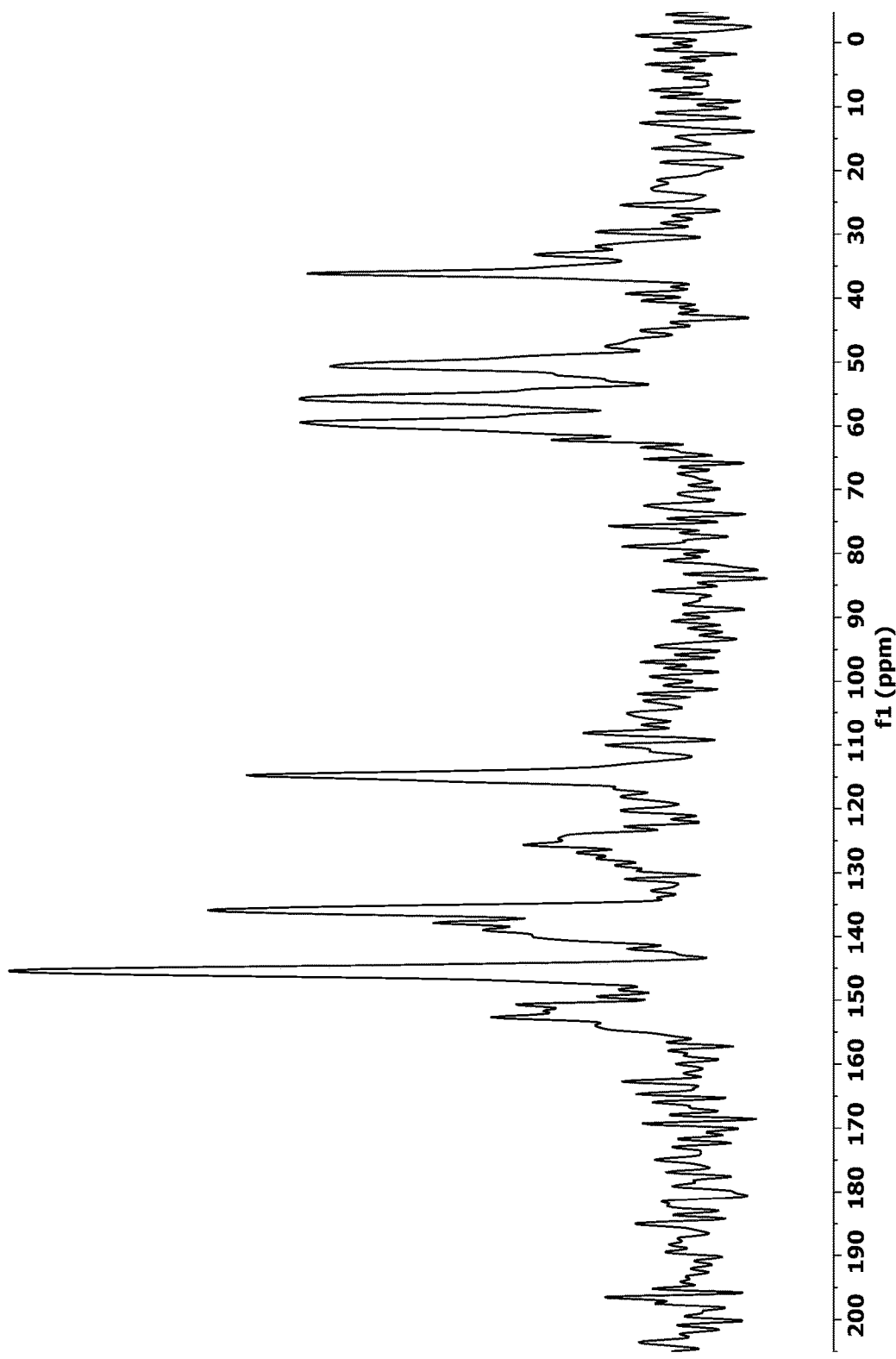
FIG. 9: $^{13}$C CP/MAS NMR spectrum of form F.

XRPD pattern, SS-NMR spectrum and TGA curve was measured using the methods described above and the results of the measurements can be found in FIGS. 1, 6 and 7 respectively.

The invention claimed is:

1. Crystalline compound 1-(8-bromopyrido[2,3-e][1,2,4] triazolo [4,3-a]pyrazin-4-yl)-N-methylazetidin-3-amine hydrogen sulfate monohydrate characterized by one or more XRPD reflections at approximately (° 2θ) 8.4; 14.7 and 17.0 (±0.2 degrees).

2. Crystalline compound of 1-(8-bromopyrido[2,3-e][1,2, 4]triazolo [4,3-a]pyrazin-4-yl)-N-methylazetidin-3-amine hydrogen sulfate monohydrate characterized by one or more XRPD reflections at approximately (°2θ) 8.4, 11.9, 14.7, 15.1 and 17.0 (±0.2 degrees).

3. Crystalline compound of 1-(8-bromopyrido[2,3-e][1,2, 4]triazolo[4,3-a]pyrazin-4-yl)-N-methylazetidin-3-amine hydrogen sulfate monohydrate characterized by one or more XRPD reflections at approximately (°2θ) 8.4, 11.9, 14.7, 15.1, 17.0, 23.0 and 24.0 (±0.2 degrees).

4. The crystalline compound according to claim 1, wherein the crystalline compound has an XRPD pattern according to the XRPD pattern in FIG. 1.

5. The crystalline compound according to claim 1, wherein the crystalline compound is characterized by a solid state 13C CP/MAS NMR spectrum with peaks at one or more of 151.5, 150.6, 145.7, 138.8, 136.1, 126.6, 125.4, 115.7, 59.7, 54.5, 50.7, 36.0 and 32.9 ppm±0.2 ppm.

6. The crystalline compound according to claim 5 characterized by having a 13C CP/MAS NMR spectrum according to the 13C CP/MAS NMR spectrum in FIG. 6.

7. The crystalline compound according to claim 1 which has a TGA curve comprising an event with an onset at about 90° C. (±10° C.).

8. The crystalline compound according to claim 1, characterized in that (i) the molar ratio of 1-(8-bromopyrido[2,3-e][1,2,4]triazolo[4,3-a]pyrazin-4-yl)-N-methylazetidin-3-amine to hydrogen sulfuric acid is in the range of from 1:0.8 to 1:1.2, or/and (ii) the molar ratio of 1-(8-bromopyrido[2,3-e][1,2,4] triazolo[4,3-a]pyrazin-4-yl)-N-methylazetidin-3-amine hydrogen sulfate to water is in the range from 1:0.8 to 1:1.2.

9. A pharmaceutical composition comprising a crystalline compound according to claim 1 and a pharmaceutically acceptable carrier.

10. A method for treating a disease selected from atopic dermatitis, itch, pruritus, and various forms of urticaria, comprising:

administering to a subject in need thereof a therapeutically effective amount of the crystalline compound of claim 1.

11. The method according to claim 10, wherein the forms of urticaria are chronic idiopathic urticaria subtypes.

12. The method according to claim 11, wherein the chronic idiopathic urticaria subtype is cholinergic urticaria.

* * * * *